(12) United States Patent
Dam-Huisman

(10) Patent No.: US 11,486,755 B2
(45) Date of Patent: Nov. 1, 2022

(54) FLOAT-BASED FLUID LEVEL INDICATOR FOR SURGICAL CASSETTE

(71) Applicant: Crea IP B.V., Vierpolders (NL)

(72) Inventor: Adriaantje Coliene Dam-Huisman, Delfgauw (NL)

(73) Assignee: Crea IP B.V., Vierpolders (NL)

( * ) Notice: Subject to any disclaimer, the term of this patent is extended or adjusted under 35 U.S.C. 154(b) by 171 days.

(21) Appl. No.: 16/762,159

(22) PCT Filed: Oct. 23, 2018

(86) PCT No.: PCT/NL2018/050700
§ 371 (c)(1),
(2) Date: May 7, 2020

(87) PCT Pub. No.: WO2019/093881
PCT Pub. Date: May 16, 2019

(65) Prior Publication Data
US 2020/0348164 A1 Nov. 5, 2020

(30) Foreign Application Priority Data
Nov. 10, 2017 (NL) ...................................... 2019886

(51) Int. Cl.
*G01F 23/66* (2006.01)
*A61M 1/00* (2006.01)

(52) U.S. Cl.
CPC ......... *G01F 23/665* (2013.01); *A61M 1/0058* (2013.01); *A61M 1/85* (2021.05)

(58) Field of Classification Search
CPC ........ G01F 23/665; G01F 23/66; G01F 23/64; G01F 23/30
See application file for complete search history.

(56) References Cited

U.S. PATENT DOCUMENTS

| | | | | |
|---|---|---|---|---|
| 1,900,433 A | * | 3/1933 | De Orlow | ............... G01F 23/66 73/314 |
| 3,685,517 A | | 8/1972 | Reynolds et al. | |
| 4,256,109 A | | 3/1981 | Nichols | |
| 5,242,434 A | * | 9/1993 | Terry | .................... A61M 1/882 604/326 |

(Continued)

FOREIGN PATENT DOCUMENTS

CH 345421 A 3/1960
WO 2016/122790 A1 8/2016

*Primary Examiner* — David Z Huang
(74) *Attorney, Agent, or Firm* — N.V. Nederlandsch Octrooibureau

(57) ABSTRACT

A fluid level indicator (50) for indicating the fluid level in an ophthalmic irrigation and/or aspiration system comprises a chamber (10) configured for holding a surgical fluid (F). The chamber (10) comprises at least one fluid port (72; 74) and a pressure port (71) for connection to a pressure source (20). A channel (140) extends from the chamber (10). The fluid level indicator (50) comprises a float (160) having a float body (162) disposed within the chamber (10) and a stem (164) extending from the float body (160) into the channel (10). The float body (160) is configured to move with the level of fluid within the chamber (10), thereby moving the stem (164) along the channel (140) extending from the chamber (10). The position of the stem (164) within the channel (40) indicates the fluid level within the chamber (10).

20 Claims, 6 Drawing Sheets

(56) References Cited

U.S. PATENT DOCUMENTS

| | | | | |
|---|---|---|---|---|
| 5,885,240 A | * | 3/1999 | Bradbury | A61M 1/0023 |
| | | | | 604/4.01 |
| 2010/0036333 A1 | | 2/2010 | Schenk et al. | |
| 2015/0297779 A1 | * | 10/2015 | Conroy | G08B 21/182 |
| | | | | 239/74 |

* cited by examiner

FLOAT-BASED FLUID LEVEL INDICATOR FOR SURGICAL CASSETTE

FIELD OF THE INVENTION

The present invention relates to a float-based fluid level indicator, in particular a float-based fluid level indicator for a surgical cassette, e.g. an irrigation or aspiration cassette for use in (ophthalmic) surgery.

BACKGROUND ART

During ophthalmic surgery, fluid is typically infused into the eye and aspirated therefrom. Systems for carrying out such surgery generally comprise aspiration and/or irrigation chambers for holding a quantity of fluid to be delivered to or from the eye. The quantity of fluid held in the chamber buffers variations caused by the pressure generation means. For the chamber act effectively, the fluid level within the chamber must be monitored—the chamber must be neither completely filled nor completely empty. For this reason, aspiration/irrigation cassettes generally comprise systems for measuring the fluid level within the chamber.

U.S. Pat. No. 5,747,824 A1 describes an apparatus and method for sensing the level of a fluid within a surgical cassette reservoir. The system comprises an array of infrared LEDs and an array of four phototransistor receivers with each LED and phototransistor mounted inside a light baffle. The light from each LED impinges upon the corresponding receiver unless blocked by the liquid/air interface. Therefore, the position of the fluid/air interface (and thus the fluid level within the reservoir) can be determined.

SUMMARY OF THE INVENTION

The present invention seeks to provide an improved arrangement for indicating the fluid level within a chamber of a surgical cassette, which allows remote sensing of the fluid level, i.e. away from the fluid/air interface.

According to a first aspect of the present invention, there is provided a fluid level indicator for indicating the fluid level in an irrigation and/or aspiration apparatus, more specifically in an ophthalmic irrigation and/or aspiration apparatus. The indicator comprises a chamber configured for holding fluid, the chamber comprising: at least one fluid port and a pressure control port for connection to a pressure source. A channel extends from the chamber. A float comprises a float body disposed within the chamber and a float stem extending from the float body and disposed at least partially within the channel extending from the chamber. The float body is configured to move with the level of fluid within the chamber, thereby moving the float stem along the channel extending from the chamber.

The float-based fluid level indicator of the present invention advantageously allows fluid level detection remote from the fluid surface, thereby providing a system which is generally insensitive to changes in liquid properties within the chamber, e.g. contamination of the fluid within the chamber with blood, eye tissue, oil and perfluorocarbon liquid (PFCL).

Further embodiments are described in the claims as attached.

SHORT DESCRIPTION OF DRAWINGS

The present invention will be discussed in more detail below, with reference to the attached drawings, in which.

DESCRIPTION OF EMBODIMENTS

Exemplary embodiments of the present invention will now be described in detail. The skilled person will understand that devices and methods described herein are non-limiting exemplary embodiments and that the scope of protection is defined by the claims. For example, although the present invention is described with respect to ophthalmic aspiration and/or irrigation procedures, the skilled person will understand that the present invention may be used in other applications, for example in other aspiration and/or irrigation systems, e.g. fine needle aspiration procedures. The skilled person will also understand that the features illustrated or described in connection with one exemplary embodiment may be combined with features described in other exemplary embodiments. Such modifications and variations are included within the scope of the present disclosure.

Figure 1:
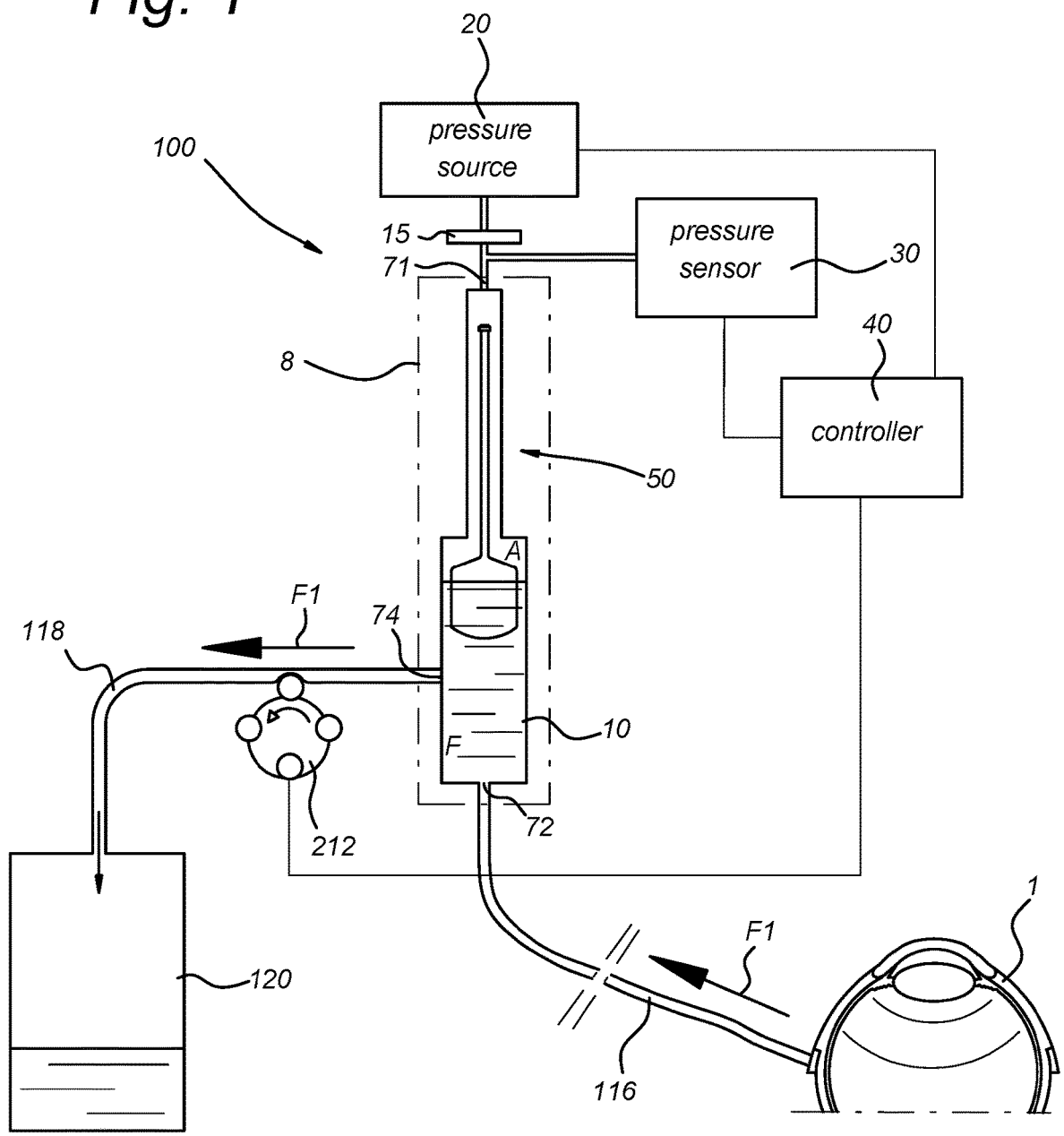
FIG. 1 shows an aspiration system for aspirating fluid and ocular material from the eye during an ophthalmic surgical procedure.
Figure 2:
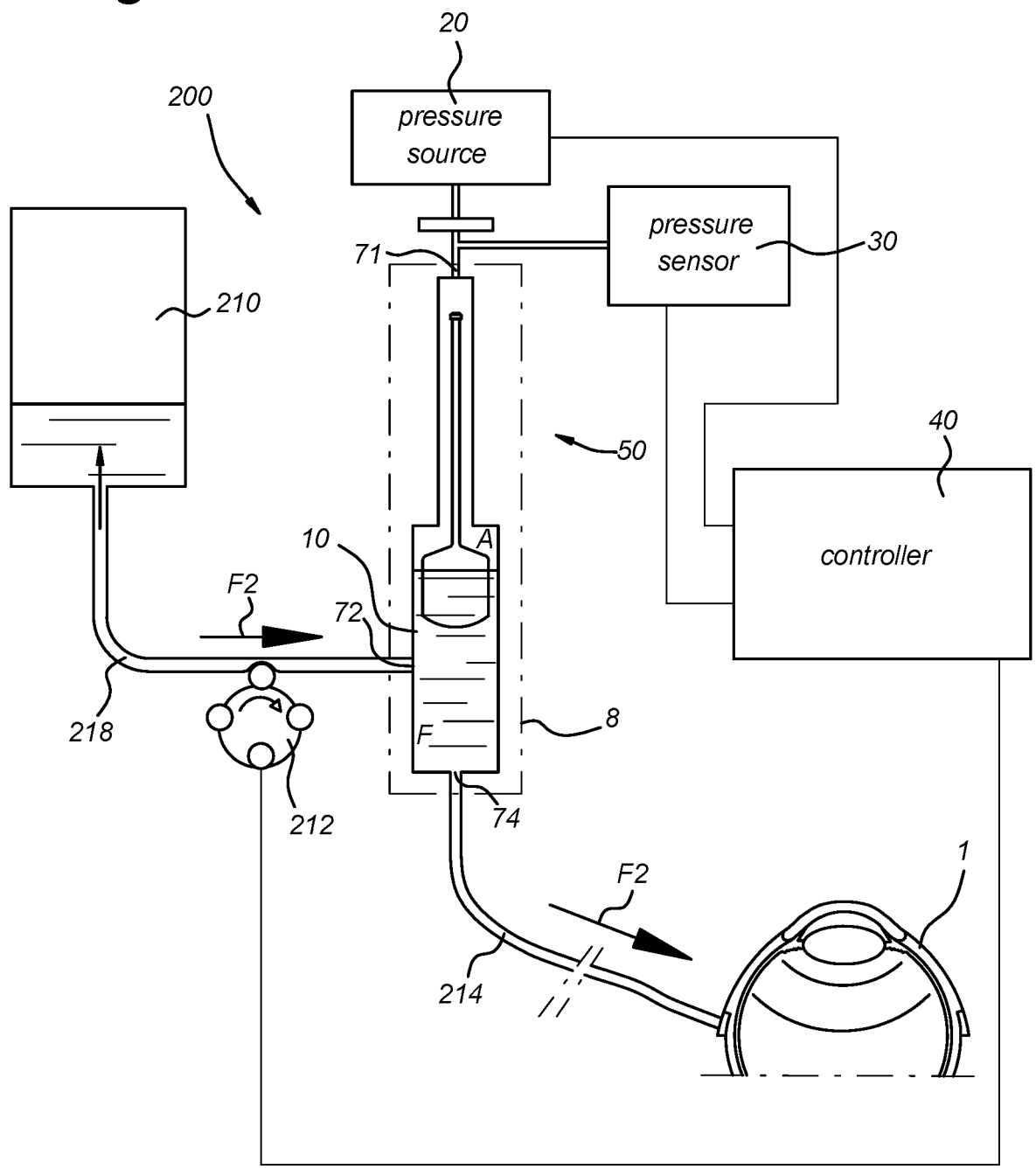
FIG. 2 shows an irrigation system for irrigating the eye during an ophthalmic surgical procedure.

The present invention may be employed in an aspiration system as shown in FIG. 1 or an irrigation system, as shown in FIG. 2. As shown in FIGS. 1 and 2, an aspiration system 100 and an irrigation system 200 according to embodiments of the present invention each comprise a cassette 8 having a chamber 10 configured to store a fluid F in a lower part of the chamber 10 and air A in the remaining space at the top of the chamber 10. The chamber 10 comprises a fluid inlet port 72, a fluid outlet port 74 and a pressure port 71. A fluid level indicator arrangement 50 is configured to indicate the level of fluid F within the chamber 10. A variable pressure source 20 is coupled to the chamber 10 via the pressure port 71 to control the pressure within the chamber 10 and thus the flow of fluid between the chamber 10 and the eye 1. A pump 212 moves fluid into and out of the chamber 10 as required.

In the aspiration system 100 shown in FIG. 1, the variable pressure source 20 is configured as a negative pressure source for drawing fluid into the chamber 10 through at least one fluid port 72, 74. The at least one fluid port 72, 74 is in fluid communication with an aspiration conduit 116 for delivering fluid from the eye 1 to the chamber 10 and a drain conduit 118 for delivering fluid F from the chamber 10 to a drain 120. The fluid is moved from the chamber 10 to the drain 120 using pump 212. In the aspiration system 100, the fluid F moves in the direction of arrow F1 in FIG. 1.

In an irrigation system 200, the pressure source 20 is configured as a positive pressure source adapted to deliver fluid F from the chamber 10 to the eye 1. In these embodiments, at least one fluid port 72, 74 is in fluid communication with an infusion conduit 218 for delivering fluid from an infusion source 210 to the chamber 10. The at least one fluid port 72, 74 is also in fluid communication with an irrigation conduit 214 for delivering fluid F from the chamber 10 to the eye 1. The fluid is moved from the infusion source 210 to the chamber 10 using pump 212. In the irrigation system 200, fluid moves in the direction of arrow F2 in FIG. 2.

The variable pressure source 20 can be configured to apply a positive pressure and a negative pressure to the chamber 10. This arrangement is advantageously versatile and can be used in both irrigation and aspiration procedures. In exemplary embodiments, the cassette 8 may further comprise a pressure sensor 30, which is provided in fluid communication with the chamber 10 to measure the pressure within chamber 10.

A controller 40 in communication with the pressure sensor 30 and the fluid level indicator 50 is configured to control the pressure and the fluid level within the chamber 10.

In further embodiments, the fluid inlet port 72 and fluid outlet port 74 are combined as a single fluid port directly connected to the chamber 10. The fluid port 72; 74 then splits into an input connection to a first conduit (such as aspiration conduit 116 in the FIG. 1 embodiment or infusion conduit 218 in the FIG. 2 embodiment), and an output connection to a second conduit (drain conduit 118 in the FIG. 1 embodiment or irrigation conduit 214 in the FIG. 2 embodiment). This is possible as the chamber 10 controls the flow of fluid into or out of the fluid port 72; 74 by pressure control.

Figure 3:
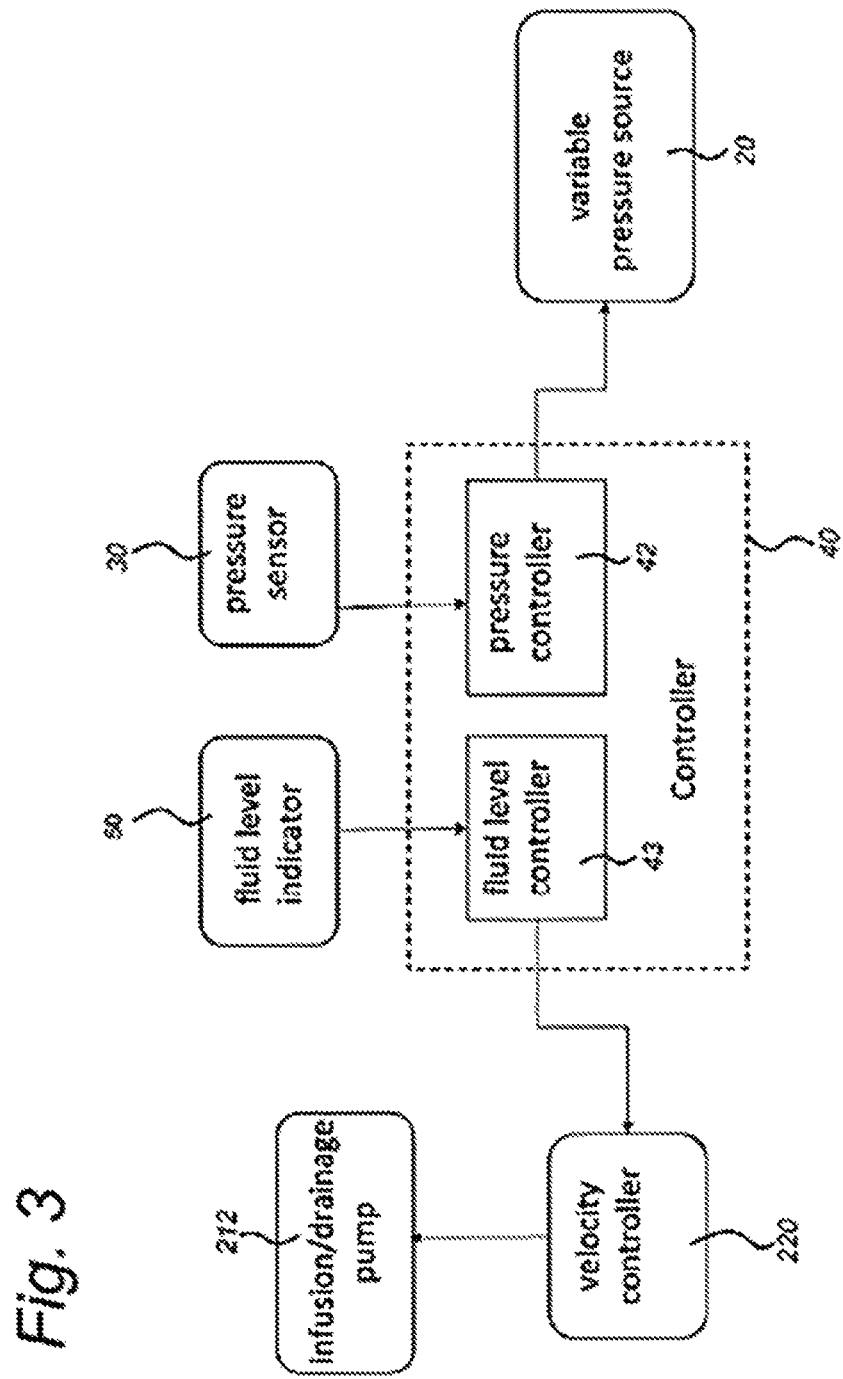
FIG. 3 shows a schematic of the controller employed in the system of FIGS. 1 and 2.

Referring now to FIG. 3, the controller 40 comprises a fluid level controller 43 for maintaining the fluid level within chamber 10 with a desired range and a pressure controller 42 for maintaining a desired pressure within the chamber 10 (e.g. the irrigation pressure or the aspiration pressure).

The fluid level controller 43 receives fluid level information from the fluid level indicator 50 and provides a set-point to a velocity controller 220, which controls the pump 212 to maintain the fluid level within chamber 10 within a desired range. In aspiration applications, the velocity controller 220 controls the rate at which fluid F is drained from the chamber 10 into the drain 120. If the controller 40 determines based on feedback from the fluid level indicator 50 that the fluid level within the chamber 10 is too high, the controller 40 adjusts the set point of the velocity controller 220 to increase the rate at which pump 212 moves fluid F from the chamber 10 to the drain 120.

In aspiration applications, the velocity controller 220 controls the rate at which fluid F enters the chamber 10 from the infusion bottle 210. If, based on feedback from the fluid level indicator 50, the controller 40 determines that the fluid level within the chamber 10 is too low, the controller 40 adjusts the set-point of the velocity controller 220 to increase the rate at which pump 212 delivers irrigation fluid from the infusion bottle 210 to the chamber 10. The pump 212 may be a peristaltic pump of the type known in the art.

The pressure controller 42 receives pressure information from the pressure sensor 30 and adjusts the pressure delivered by the variable pressure source 20 to maintain the pressure within the chamber 10 at the desired level.

Advantageously, the controller 40 shown in FIG. 3 can also allow for calculation of the flow rate to and from the eye 1 without the need for a flow sensor within the aspiration line 116 or the irrigation line 214. This is advantageous because ophthalmic surgical systems generally comprise narrow gauge irrigation/aspiration lines, across which flow sensing can be challenging. However, in the systems described above, the controller 40 can calculate the flow rate to or from the eye based on all or some of the following known quantities: the fluid level within the chamber (measured by fluid level indicator 50); the pressure within chamber 10 (measured by pressure sensor 30); and the flow rate dictated by the pump 212 to and from the chamber 10, system parameters relevant for pressure losses in the flow to/from the eye during use (e.g. tubing and needle length and diameters).

The above description of FIG. 3 relates to a pressure mode of operation, wherein a user can input a set point for the desired pressure to pressure controller 42. This may be applied both when the present invention embodiments are used for controlling irrigation to the eye, and for controlling aspiration from the eye. In a further embodiment, specifically suited for aspiration purposed, the present invention embodiments are operated in a flow control mode. In the flow control mode, a set point for the desired aspiration flow is input to the velocity controller 220, for controlling the speed of the drainage pump 212. The fluid level controller 43 uses the input from the fluid level indicator 50 to provide a pressure set point to the pressure controller 42 that subsequently control the variable pressure source 20 to ensure the fluid level is controlled to an internal defined set point.

It will be appreciated that for the system to act effectively, the chamber 10 must be neither completely full nor completely empty. This is because the fluid F in the chamber 10 provides a buffer for fluctuations in the pressure and fluid (liquid) flow delivered by the pressure source 20, the pump 212 and occlusions in the aspiration or irrigation lines. Therefore, the fluid level indicator arrangement 50 must allow accurate sensing of the fluid level within the chamber.

Figure 4A:
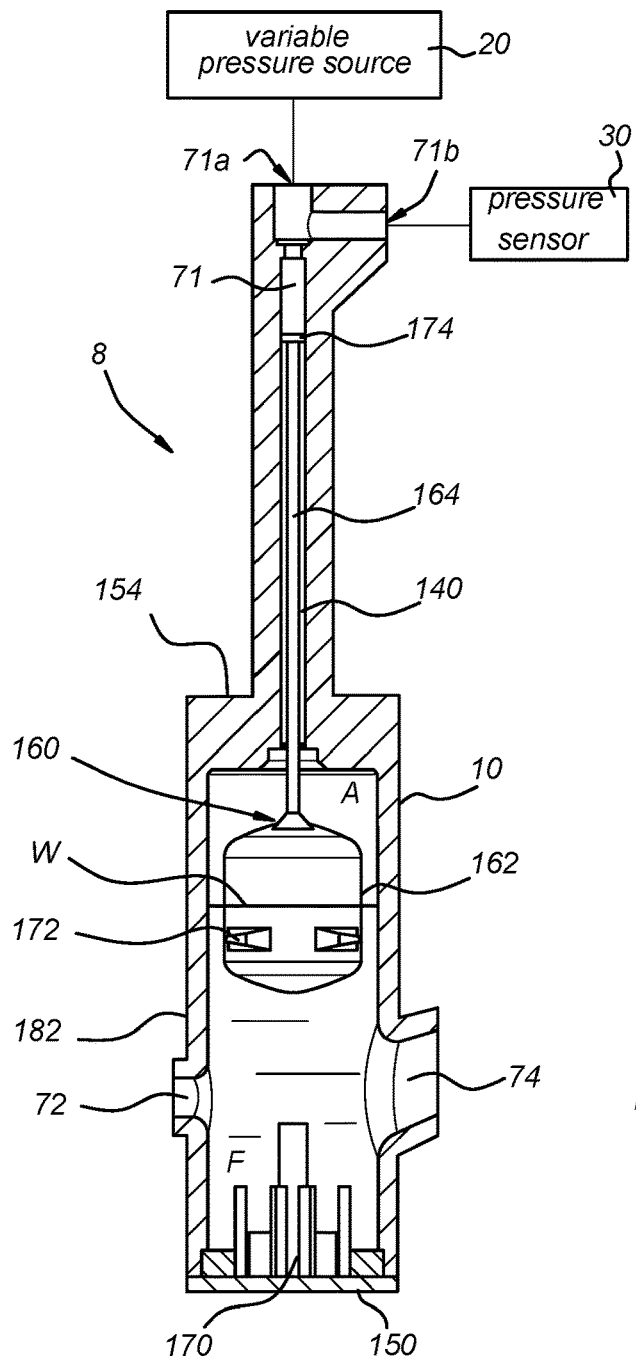
FIGS. 4A and 4B show a float based fluid level indicator for indicating the level of fluid within a chamber of a surgical irrigation system or a surgical aspiration system, in accordance with an embodiment of the present invention.

As shown in FIG. 4A, the cassette 8 includes a float-based fluid level indicator arrangement 50 for indicating the fluid level in an (ophthalmic) irrigation and/or aspiration system. The fluid level indicator 50 is provided in chamber 10, which (as described above) comprises at least one fluid port 72; 74 and a pressure port 71 configured for connection to the pressure source 20 In the exemplary embodiment shown in FIG. 4A, the fluid port comprises a fluid inlet port 72 for connection to a first conduit (e.g. aspiration line 116 or infusion line 218) and a fluid outlet port 74 for connection to a second conduit (e.g. drainage conduit 118 or irrigation conduit 214). A channel 140 extends from the chamber 10. Disposed within the chamber 10 is at least one float 160, which is configured to rise and fall with the fluid level W within the chamber 10. The float 160 comprises a float body 162, which is disposed within the chamber 10 and a float stem 164, which extends from the float body and is disposed at least partially within the channel 140 extending from the chamber 10.

The float body 162 and the float stem 164 are arranged such that they are free to move within the chamber 10 and channel 140 respectively, as the fluid level W rises and falls. In other words, the float body 162 is configured to move with the level of fluid within the chamber 10, thereby moving the float stem 164 along the channel 140 extending from the chamber 10. The cassette 8 is configured so that the position of the float stem 164 within the channel 140 can be measured by a sensing system that detects the position of the float stem 164 within the channel 140. The fluid level W within the chamber can thus be determined by measuring the position of the float stem 164 within the channel 140. By measuring the position of the float stem 164 within the channel 140, the level of the fluid F within the chamber 10 can be made indirectly, i.e. remote from the air/liquid interface W within chamber 10. This is advantageous because such a measurement is generally insensitive to changes in liquid properties within the chamber 10 which may affect the liquid surface, e.g. contamination of the fluid F with blood, eye tissue, oil and perfluorocarbon liquid (PFCL).

As mentioned above, the fluid port 72; 74 can comprise a single fluid port configured to be connected to a first fluid conduit and a second fluid conduit. Alternatively, the at least one fluid port can comprise a first fluid port 72 configured to be connected to a first fluid conduit and a second fluid port 74 configured to be connected to a second fluid conduit. In either case, the first and second conduits provide fluid flow towards and away from the chamber 8 respectively.

The float stem 164 is part of the float 160, and serves a number of purposes, including but not limited to guiding the float 160 along a single direction (up and down in the embodiments shown in the FIGS. 1, 2, 4A, 5A and 6). The float stem 164 also serves to allow remote measurement of the water level in the chamber 10, and for this the float stem 164 can be embodied as a long thin element. This also reduces the weight of the part of the float 160 above the liquid level, allowing a quick and highly dynamic measurement of the liquid level in the chamber 10. The float stem 164 also allows to minimise the dimensions of the channel 140, in order to have as little volume of air between the pressure port 71 and the chamber 10, and to allow a proper and secure guidance of the float 160. As will be explained below with reference to FIG. 4B, the float stem 160 and channel 140 may also be arranged to prevent rotation of the float 160 in the chamber 10 and channel 140.

As shown in FIG. 4A, the chamber 10 comprises a base 150, at least one sidewall 152 and a top wall 154. The channel 140 extends from the top wall 154 of the chamber 10, in the embodiment shown the channel 140 thus extends in a vertical direction.

The base 150 of the chamber 10 may further comprise at least one guide feature 170, of which one function is to guide the float body 162 into a predetermined location position within the chamber 10. For example, the at least one guide feature 170 may locate the float body 162 within the chamber 10 such that the float stem 164 is positioned centrally within the channel 140. In an alternative embodiment of the invention, the guide features 170 can be provided on the sidewalls 152 of the chamber 10. The guide features 170 can take the form of a series or ribs or guide members extending into the chamber 10, which confine the float 160 to the central region of the chamber 10, at least when the float body 162 is located in the lower part of the chamber 10. As shown in FIG. 4A, the guide features 170 may extend vertically from the base 150 of the chamber 10 partway to the top wall of the chamber 154, such that the float 162 is seated centrally within the chamber when the fluid level W is in the lower part of the chamber 10. However, the skilled person will appreciate that in some embodiments the guide features 170 can extend between the base 150 and the top wall 154 of the chamber.

The guide features 170 described above can be advantageously employed in further functionalities, e.g. to centre the float stem 164 within the channel 140. This minimises the risk of the float stem 164 becoming jammed in the channel 140, which could lead to inaccurate or delayed fluid level measurements. The guide means 170 may also advantageously prevent the float body 160 sticking to the sidewalls 152 of the chamber by virtue of capillary forces or adhesion, e.g. due to viscous fluids that enter the chamber 10.

Guide features 170 in the lower part of the chamber 10 can be particularly advantageous when either or both of the fluid inlet port 72 or the fluid outlet port 74 are provided in the lower part of the chamber 10. In such embodiments, the at least one guide feature 170 can locate the float body 164 within the chamber 10 above the fluid port(s) 72; 74, such that occlusion of fluid inlet port 72 and/or the fluid outlet port 74 is prevented. Furthermore, such an arrangement would also ensure that fluid flow around the guide features 170 is dampened, preventing turbulence (and consequently keeping possibly present debris in the fluid at the bottom of the chamber 10).

Figure 4B:
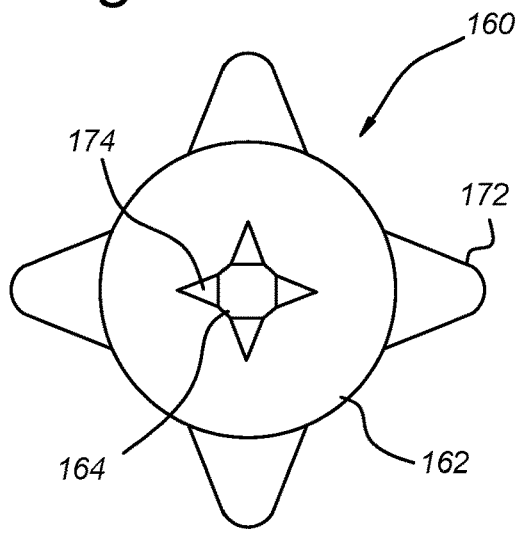

FIG. 4B shows a top view of a float 160 according to one embodiment of the invention. As shown in FIG. 4B, at least one of the float body 162 and the float stem 164 can comprise one or more projections 172, 174, which allow to position the float 160 within the chamber 10 with respect to its longitudinal axis (e.g. keeping the float 160 centred or keeping the float 160 in a constant off-centre position). In the embodiment shown in FIG. 4B, the float body 162 comprises radially extending projections 172 around the circumference of the float body 162. The projections 172 are configured to limit lateral movement of the float body 162 within the chamber 10 and prevent the float body 162 from coming into close contact with the sidewalls of the chamber 10. The projections 172 improve the sensitivity of the float based fluid level indicator 50 because they prevent the float 160 from tilting within the chamber 10 and minimise the risk of capillary forces between the float 160 and the inner surfaces of the chamber 10 or channel 140 from interfering with movement of the float 160 as the fluid level W rises and falls. The skilled person will appreciate that the projections 172 may also help to locate the float body 162 centrally within the chamber 10, such that occlusion of the fluid inlet port 72 and/or the fluid outlet port 74 is prevented. The skilled person will appreciate that the projections 172 and guide features 170 can be used alone or in combination with each other to achieve this goal.

Additionally, or as an alternative to the projections 172 provided on the float body 162, the float 160 may comprise projections 174 on the stem 164. The projections 174 limit lateral movement of the float stem 164 within the channel 140 and prevent unwanted capillary forces between the float stem 164 and the channel 140 (should fluid enter the channel 140) and maintain a stiff coupling between the fluid level W within the chamber 10 and the position of the stem 164 within the channel 140, thereby improving the sensitivity of the fluid level indicator 50. Furthermore, the projections 174 ensure that rotation of the float 160 around its three rotational axes is restricted.

The fluid level indicator 50 can be configured to prevent rotation of the float 160 within the cassette 8. For example, the guide means 170 can cooperate with the projections 172 on the body 162 of the float 160 to limit rotation of the float 160 about its longitudinal axis.

Additionally, or as an alternative, the channel 140 and/or the stem 164 can be configured to prevent rotation of the float stem 164 within the channel 140. In a further embodiment this may even relate to preventing rotation in all three (orthogonal) rotation axes, allowing only up and down movement along the longitudinal axis of the float 160. For example, the channel 140 may be provided with ribs or grooves to cooperate with the projections 174 to limit rotation of the float stem 164 within the channel 140. This can be useful for correctly orienting the float stem 164 within the channel 140 to facilitate position measurement (discussed further with reference to FIGS. 5A and B. The skilled person will appreciated that the float stem 164 may also be oriented within the channel 140 in other ways. For example, the channel 140 and the float stem 164 may be formed with a non-circular cross section, which prevents rotation of the float stem 164 within the channel 140.

The skilled person will appreciate that the geometry of the float 160, the projections 172, 174 and the chamber 10 can be optimized with respect to each other to create a stiff coupling between the fluid level within the chamber 10 and the float 160. This prevents tilting of the float 160 within the chamber 10 and maximises sensitivity of the fluid level indicator 50.

As shown in FIG. 4B, the float stem 164 is relative narrow compared to the float body 162 and the channel 140 is relatively narrow compared to the chamber 10. In other words, a cross sectional surface of the stem 164 (perpendicular to its longitudinal direction) is smaller than a cross sectional surface of the float body 162, and a diameter of the channel 140 is smaller than a diameter of the chamber 10. This advantageously minimizes the combined volume of the channel 140 and the chamber 10 and provides for fast pressure control within the chamber 10. In an alternative embodiment, the chamber 10 and channel 140 may have substantially similar cross sectional dimensions.

In the embodiment shown in FIG. 4B, the float stem 164 has a polygonal shape. In further alternative embodiments, the channel 140 and float stem 164 have corresponding cross sectional shapes, such as cylindrical, elliptical, square, rectangular, etc.

In relation to all embodiments described herein, the shape of the float 160 and chamber 10 can be optimized. More in particular, an aspect ratio between the cross-sectional area of the float 160 (for the part at the liquid-air interface) and the 'open-water' area between the float 160 and the inner wall of the chamber 10 is selected to be as high as possible. The larger the ratio float area to open-water area is, the better the float 160 will function in terms of stiffness (i.e. the float 160 will better indicate the actual liquid level in the chamber 10 (smaller liquid volume changes can be measured). However, if the float 160 comes to close to the inner wall of the chamber 10, capillary forces may become apparent and will attract the float 160 towards the inner wall resulting in an increased friction force for the up/down movement of the float 160. Therefore a gap between float 160 and inner wall of the chamber 10 is provided, e.g. of at least 1 or at least 2 mm.

Furthermore, a smaller total volume of the chamber 10 will increase the sensitivity of the fluid level sensor 50 (i.e. a small liquid volume change results in a high float position change), but here a trade-off has to be made with respect to possible flow variations and the available fluid level measurement range. E.g. if the user in operation aspirates liquid, but suddenly pulls out the needle from the eye and keeps it in air while keeping aspiration turned on, a fast increase in flow rate will occur (as viscosity of air is about 50 times smaller than viscosity of the aspiration fluid), and as a result the float 160 will move upwards rapidly.

In some embodiments, the chamber 10 has a small air volume (i.e. less than 10 cc). However, the skilled person understands that the chamber 10 may have any air volume for which the control is needed. Note that the air volume is the volume of air within the chamber 10 during normal operation, i.e. when the chamber 10 is filled with fluid within the target range. The target volume of fluid may be 10-15 cc. which would still allow a fast priming (i.e. filling the cassette 8 and all connecting lines with fluid), and maintain a high dynamic response. The variation in amount of fluid in the chamber 10 during operation is e.g. about 3 cc, which would also still enable proper and accurate level sensing using the fluid level indicator 50. In an exemplary embodiment, the total internal volume of the chamber 10 is about 25-30 cc.

In an exemplary embodiment of the invention, the chamber 10 can be arranged to allow condensation to form within the chamber 10 but not within the channel 140. This minimises the risk of condensation affecting the fluid level measurement (e.g. due to the float 160 sticking within the channel 140 and/or due to droplets forming within the channel 140 that disrupt measurement of the position of the stem 164 within the channel 140). For example, the chamber 10 can be modified such that condensation is localized on distinct regions within the chamber 10 near the liquid-air interface, but minimized in the channel 140. This can also be accomplished by using specific (local) environmental control (pressure and temperature. In an equilibrium circumstance, the humidity level in the upper part of the chamber 10 will be high (100%). By increasing pressure, condensation will primarily occur at the top end of the chamber 10 (and not in the channel 140), and by lowering the temperature, condensation will occur just above the fluid level and thus not in channel 140.

The location of the pressure port 71 is such that if the absolute pressure in the chamber 10 needs to be increased the additional air enters via the channel 140 into the chamber 10. The air that is already present (also in the channel 140) and has a high relative humidity is pushed/displaced into the chamber 10. Therefore compression of this high humidity air takes place in the chamber 10 where consequently condensation occurs. The added air (which has a low(er) relative humidity is inserted in the channel part 140 and does not condense (it originates from a variable pressure source that is at higher absolute pressures so the relative humidity will always be lower.

Temperature gradients in the cassette 8 are minimized and/or designed such that the temperature in the chamber 10 (near the liquid-air interface) is preferably lower than the air temperature in the other sections, such as channel 140. Note that this may be accomplished using the present invention embodiments of the position sensing system (as discussed below with reference to FIGS. 5A and B), e.g. the light source used for the position detection of the float stem 164, which will increase the temperature in the channel 140.

In at least one exemplary embodiment of the invention, the channel 140 can provide fluid communication between the variable pressure source 20 and the pressure sensor 30 and the chamber 10.

As shown in FIG. 4A, the channel 140 provides a conduit between the chamber 10 and the pressure port 71. The pressure port 71 provides fluid communication between the chamber 10 and a pressure control port 71a and a pressure sensing port 71b. The pressure control port 71a is fluidically connected to the variable pressure source 20 for pressurising the chamber 10. The pressure sensing port 71b is connected to the pressure sensor 30 for sensing the pressure within the chamber 10. This arrangement is advantageous because it reduces the number of ports required within the chamber 10. However, the skilled person will appreciate that the pressure control port 71a and/or the pressure sensing port 71b may be in fluid communication with the chamber 10 via one or more dedicated conduits that do not rely on the channel 140 and instead open directly into the chamber 10.

In embodiments in which the pressure within the chamber 10 is controlled via the channel 140, it will be appreciated that neither the float stem 164 nor the float body 162 can be allowed to block the channel 140. Therefore, the float stem 164 and the channel 140 are configured to allow air to move past the float stem 164 within the channel 140. This can be achieved, as described above, by projections 174 provided on the float stem 164 or on the walls of the channel 140, to maintain an air gap between the wall of the channel 140 and the float stem 164.

Fluid communication between the pressure port 71 and the chamber 10 is ideally maintained regardless of the position of the float 160. Therefore, in the embodiment shown in FIG. 4A, it is advantageous to provide surface features on the float body 162 or the top wall 154 of the chamber 10 that prevent a seal forming between the float 160 and the entry to the channel 140. A plurality of ribs or channels (not shown) may be formed either on the top wall 154 of the chamber 10 or the upper surface of the float body 162, to ensure that fluid (i.e. air) can pass into the channel 140 between the float body 162 and chamber wall, even if the float body 162 abuts the top wall 154 of the chamber 10. This can prevent the float 160 sealing the channel 140 of the chamber due to e.g. negative pressure in the channel 140.

Figure 5A:
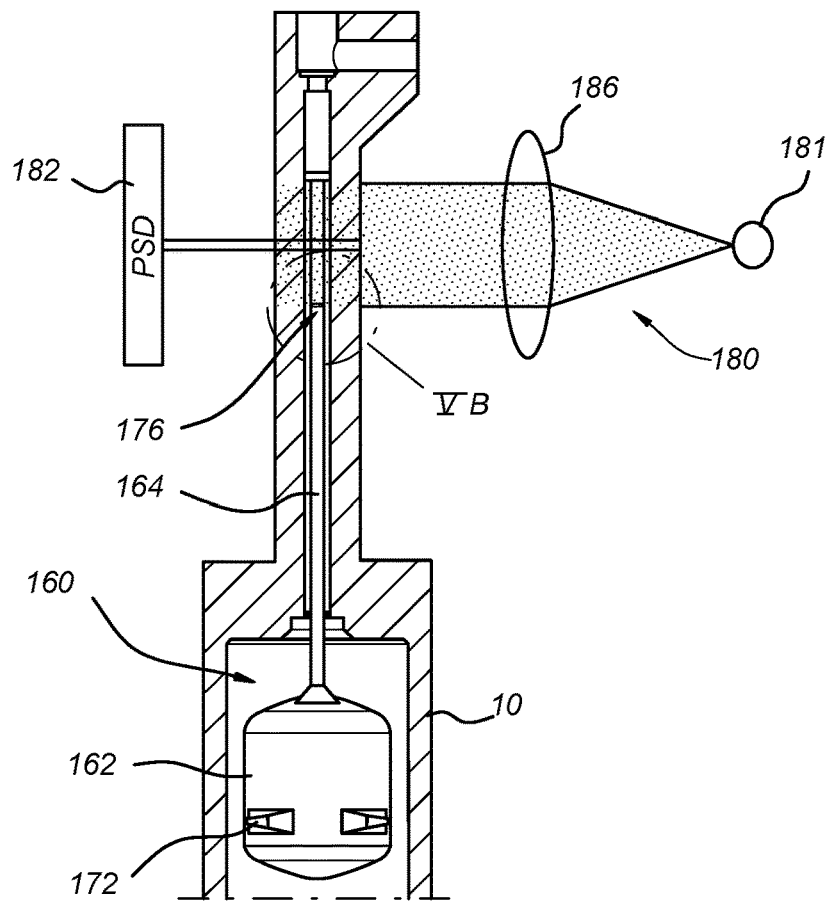
FIGS. 5A and 5B show a sensing system for use with a fluid level indicator according to an embodiment of the present invention.
Figure 5B:
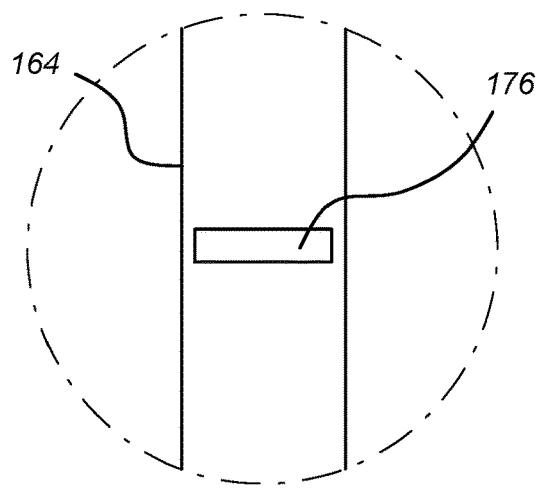

As shown in FIGS. 5A and 5B, the fluid level indicator 50 described above can be combined with an automated fluid level sensing system, which comprises one or more sensors for detecting the position of the float stem 164 within the channel 140.

As shown in FIG. 5B, the position sensing system is configured to detect the position of a marker (e.g. a slit), provided on the float stem 164, allowing sensing the liquid level W in the chamber 10 remotely from the liquid surface therein.

In the exemplary sensing system illustrated in FIGS. 5A and 5B, the position sensing system comprises an optical sensing system 180 configured to measure the position of the marker 176. The optical sensing system 180 comprises a light source 181 (e.g. a collimated light source) arranged on a first side of the channel 140 and at least one optical sensor 182 (e.g. a position sensitive sensor or "PSD") arranged on an opposite side of the channel 140. The channel 140 separates the light source 181 and the PSD 182 and is formed of a transparent material. The marker 176 e.g. comprises an aperture (either in the form of a slit as shown in FIG. 5B, or alternatively, in the form of an upper edge of the float stem 164) configured to allow light from the light source to pass there through to impinge upon the at least one optical sensor 182 on the opposite side of the channel. Advantageously, the slit can be a horizontal slit (i.e. perpendicular to the longitudinal axis of the stem 164), which is formed as an aperture or as a region of transparent material in an otherwise opaque stem.

The PSD 182 and the light source 181 are arranged such that collimated light from the light source 181 passes through the cassette 8 and the channel 140 and impinges upon the PSD 182. However, the opaque stem 164 prevents collimated light from the light source 181 from impinging on the PSD except in the region of the slit 176. Since only the slit 176 allows transmission of light from the light source 181 through the stem 164 and onto the PSD 182, after calibration, the electrical signal from the PSD can be used to indicate the precise position of slit 176 and thus the position of float stem 164 within the channel 140. Due to the stiff coupling between the float stem 164 of the float and the fluid surface W, this provides for accurate determination of the fluid level within the chamber 10.

As shown above, the collimated light source 181 can be provided by an LED in combination with a lens 186. However, the skilled person will appreciate that other light sources may be provided. Similarly, the optical sensing system 180 described above comprises a single PSD 182. However, the skilled person will appreciate that multiple sensors may be provided to accurately detect the position of the marker 176 within the channel 140.

Moreover, the skilled person will appreciate that the present invention is not limited to the optical sensing system 180 described above. For example, the marker 176 and the sensing system 180 may be adapted for magnetic, electrical and acoustic methods for detecting the position of a float stem 164 within the channel 140. It will also be apparent to the skilled person that in some embodiments, marker 176 may be omitted and that the position of the float stem 164 within the channel 140 may be determined by determining the position of the distal tip or edge of the float stem 164.

The optical sensing system 180 described above can be incorporated into the cassette 8. However, it is envisaged that in some embodiments of the present invention, the position sensing system 180 forms part of a wider irrigation and/or aspiration apparatus and that the cassette 8 is disposable. In these embodiments, the cassette 8 includes the fluid level indicator arrangement described above, which can be employed with sensing means incorporated into a wider irrigation and aspiration system. The float-based fluid level indication arrangement described above is particularly suited to disposable cassette applications because it comprises inexpensive components to reliably indicate the fluid level within the chamber 10 of cassette 8.

In such embodiments, the cassette 8 advantageously can be provided with one or more locating features (not shown) for securing the cassette 8 (and thus the channel 140 and the stem 164) in a predetermined position relative to sensing means (e.g. light source 181 and PSD 182). This can limit or eliminate the need for repeated calibration of the sensing means. In addition to improved accuracy and rapid reaction times, the float-based fluid level indicator is also particularly suitable for disposable cassette embodiments due to the low cost of the parts required to indicate the fluid level in the chamber 10.

To allow visual inspection of the chamber 10 and to facilitate optical sensing of the fluid level via the float based fluid level indication system described above, the cassette 8 may be made of a transparent plastic material. However, the skilled person will appreciate that the cassette 8 may be formed of an opaque or translucent material, so long as the portion of the cassette comprising the channel 140 is transparent to the wavelength of light emitted by the light source 181.

Figure 6:
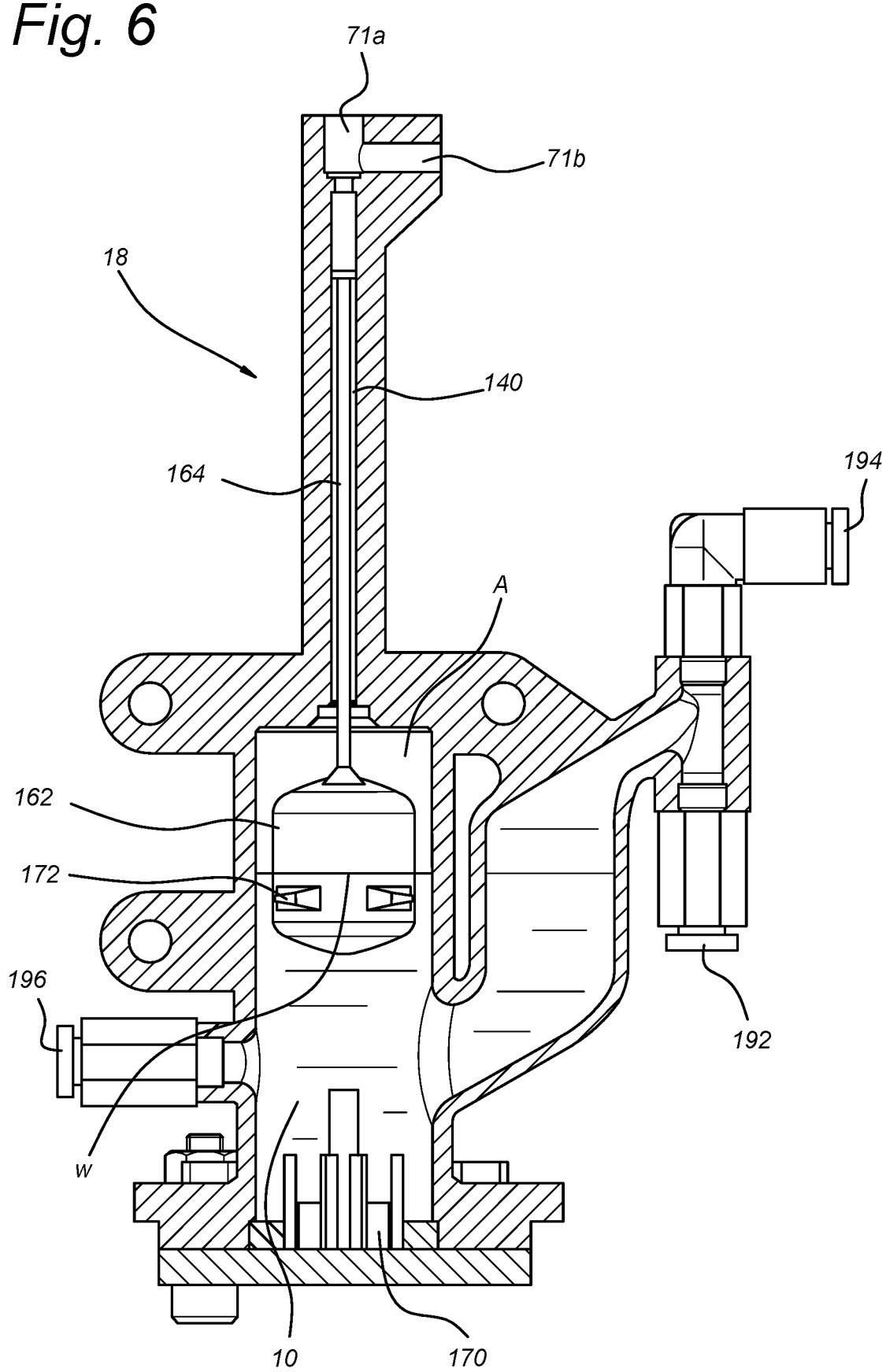
FIG. 6 shows a float based fluid level indicator provided in a multi-purpose surgical cassette suitable for use in irrigation and aspiration procedures.

Referring now to FIG. 6, the float based fluid level indicator arrangement 50 according to the present invention may be employed in an exemplary multi-function cassette 18, which is suitable for use in both aspiration and irrigation procedures. The cassette 18 is generally similar to cassette 8 described above and includes a chamber 10, a channel 140, a float 160 and at least one pressure port 71 for fluidically connecting the chamber 10 to the variable pressure source 20 and the pressure sensor 30, as described above.

The cassette 18 also comprises three fluid ports for connecting the chamber 10 to the fluid lines as described above with reference to FIGS. 1 and 2. A medical practitioner can selectively connect the fluid ports depending upon the desired application, e.g. irrigation or aspiration.

In an exemplary embodiment, the first fluid port 192 is configured for connection to an aspiration line 116 in an aspiration system (see FIG. 1) or an infusion line 218 in an irrigation system (see FIG. 2). The second fluid port 194 is configured for connection to the drainage line 118 in an aspiration system (see FIG. 1). The third fluid port 196 may be optionally present and configured for connection to an irrigation system (see FIG. 2), e.g. for easy and quick priming of the aspiration system. The second and third fluid ports 194, 196 may each comprise a valve (not shown) for closing the ports when not in use.

For use in a surgical aspiration system (as shown in FIG. 1), the first fluid port 192 is connected to an aspiration line 116 and the second fluid port 194 is connected to a drainage line 118. The third fluid port 196 is closed by the valve (not shown) during regular operation. The cassette 18 then operates as described with reference to FIG. 1.

For use in a surgical irrigation system (as shown in FIG. 2), the first fluid port 192 is connected to an infusion line 218 and the third fluid port 196 is connected to an irrigation line 214. The second fluid port 194 is closed by the valve (not shown). The cassette 18 then operates as described with reference to FIG. 2.

As described above, the multi-function cassette 18 can be used in both irrigation and aspiration procedures. This simplifies the array of components required to carry out an ophthalmic procedure and provides greater flexibility for medical practitioners.

In the exemplary embodiments described above, the fluid level indicator arrangement 50 is comprised in a surgical cassette 8. However, the skilled person will appreciate that a fluid level indicator arrangement 50 in accordance with the present invention may also be integrated within an aspiration/irrigation apparatus, i.e. such that the chamber and fluid level sensing form part of an irrigation/aspiration apparatus and are not removable.

The invention claimed is:

1. An irrigation system for use during ophthalmic surgical procedures, the irrigation system comprising:
  a fluid level indicator arrangement for indicating the fluid level in the irrigation system, the fluid level indicator arrangement comprising:
    a chamber configured for holding a fluid, the chamber comprising:
    at least one fluid port; and
    a pressure port for connection to a pressure source;
    a channel extending from the chamber;
    a float comprising:
      a float body disposed within the chamber;
      a float stem extending from the float body and disposed at least partially within the channel extending from the chamber,
      wherein the float body and/or the float stem comprises one or more radially extending projections;
  a variable pressure source in fluid communication with the pressure port;
  an irrigation conduit in fluid communication with the at least one fluid port;
  an infusion conduit in communication with the at least one fluid port; and
  a position sensing system with one or more sensors for detecting the position of the float stem within the channel;
  wherein the position sensing system is an optical sensing system comprising a light source arranged on a first side of the channel and at least one optical sensor arranged on an opposite side of the channel;
  the channel is formed of a transparent material; and
  the marker comprises an aperture configured to allow light from the light source to pass there through to impinge upon the at least one optical sensor.

2. The irrigation system according to claim 1, wherein the at least one fluid port comprises a single fluid port configured to be connected to a first fluid conduit and a second fluid conduit.

3. The irrigation system according to claim 1, wherein the at least one fluid port comprises a first fluid port configured to be connected to a first fluid conduit and a second fluid port configured to be connected to a second fluid conduit.

4. The irrigation system according to claim 1, wherein the fluid level indicator is comprised in a surgical cassette.

5. The irrigation system according to claim 1, wherein the chamber comprises a base, at least one sidewall and a top wall, and wherein the channel extends from the top wall of the chamber.

6. The irrigation system according to claim 1, wherein the channel and/or the float stem are configured to prevent rotation of the float stem relative to the channel.

7. The irrigation system according to claim 1, wherein the float stem is relatively narrow compared to the float body and the channel is relatively narrow compared to the chamber.

8. The irrigation system according to claim 1, wherein the chamber comprises at least one guide feature.

9. The irrigation system according to claim 8, wherein the at least one guide feature locates the float body within the chamber above the fluid port.

10. The irrigation system according to claim 1, wherein the chamber is arranged to allow condensation within the chamber but not in the channel to minimize interference with fluid level detection.

11. The irrigation system according to claim 1, wherein the pressure port is in fluid communication with the chamber via the channel.

12. The irrigation system according to claim 1, wherein the float stem comprises at least one marker.

13. An aspiration system for use during ophthalmic surgical procedures, the aspiration system comprising:
  a fluid level indicator arrangement for indicating the fluid level in the aspiration system, the fluid level indicator arrangement comprising:
    a chamber configured for holding a fluid, the chamber comprising:
    at least one fluid port; and
    a pressure port for connection to a pressure source;
    a channel extending from the chamber;
    a float comprising:
      a float body disposed within the chamber;
      a float stem extending from the float body and disposed at least partially within the channel extending from the chamber,
      wherein the float body and/or the float stem comprises one or more radially extending projections;
  a variable pressure source in fluid communication with the pressure port;
  a drain conduit in fluid communication with the at least one fluid port;
  an aspiration conduit in fluid communication with the fluid port; and
  a position sensing system with one or more sensors for detecting the position of the float stem within the channel;
  wherein the position sensing system is an optical sensing system comprising a light source arranged on a first side of the channel and at least one optical sensor arranged on an opposite side of the channel;
  the channel is formed of a transparent material; and
  the marker comprises an aperture configured to allow light from the light source to pass there through to impinge upon the at least one optical sensor.

14. The aspirational system according to claim 13, wherein the at least one fluid port comprises a single fluid port configured to be connected to a first fluid conduit and a second fluid conduit.

15. The aspirational system according to claim 13, wherein the at least one fluid port comprises a first fluid port configured to be connected to a first fluid conduit and a second fluid port configured to be connected to a second fluid conduit.

16. The aspirational system according to claim 13, wherein the fluid level indicator is comprised in a surgical cassette.

17. The aspirational system according to claim 13, wherein the chamber comprises a base, at least one sidewall and a top wall, and wherein the channel extends from the top wall of the chamber.

18. The aspirational system according to claim 13, wherein the channel and/or the float stem are configured to prevent rotation of the float stem relative to the channel.

19. The aspirational system according to claim 13, wherein the float stem is relatively narrow compared to the float body and the channel is relatively narrow compared to the chamber.

20. The aspirational system according to claim 13, wherein the chamber comprises at least one guide feature.

* * * * *